United States Patent
Ehrling et al.

(10) Patent No.: US 10,921,299 B2
(45) Date of Patent: Feb. 16, 2021

(54) ANALYTICAL DEVICE FOR CONSTITUENTS OF A SAMPLE

(71) Applicant: Analytik Jena AG, Jena (DE)

(72) Inventors: Christiane Ehrling, Ilmenau (DE); Heiko Henneberg, Plaue (DE)

(73) Assignee: Analytik Jena AG, Jena (DE)

( * ) Notice: Subject to any disclaimer, the term of this patent is extended or adjusted under 35 U.S.C. 154(b) by 925 days.

(21) Appl. No.: 15/428,431

(22) PCT Filed: Jul. 20, 2015

(86) PCT No.: PCT/EP2015/066507
§ 371 (c)(1),
(2) Date: Feb. 6, 2018

(87) PCT Pub. No.: WO2016/023707
PCT Pub. Date: Feb. 18, 2016

(65) Prior Publication Data
US 2018/0156762 A1    Jun. 7, 2018

(30) Foreign Application Priority Data

Aug. 12, 2014 (DE) .................. 10 2014 111 506

(51) Int. Cl.
*G01N 31/12* (2006.01)
*B01J 12/00* (2006.01)
(Continued)

(52) U.S. Cl.
CPC .............. *G01N 31/12* (2013.01); *B01J 12/00* (2013.01); *B01J 19/02* (2013.01); *B01J 19/2475* (2013.01);
(Continued)

(58) Field of Classification Search
CPC ........ B01J 12/00; B01J 19/02; B01J 19/2475; B01J 2219/0263; B01J 12/005;
(Continued)

(56) References Cited

U.S. PATENT DOCUMENTS 4,582,686 A * 4/1986 Tsuji .................. G01N 33/2022
422/80
5,689,059 A   11/1997 Oh et al.
(Continued)

FOREIGN PATENT DOCUMENTS

DE    19826496 A1   1/2000
DE    69801053 T3   1/2007
(Continued)

OTHER PUBLICATIONS

International Search Report for PCT Application No. PCT/EP2015/066507, WIPO, dated Nov. 11, 2015, 11 pp.
(Continued)

*Primary Examiner* — Samuel P Siefke
*Assistant Examiner* — Quocan B Vo
(74) *Attorney, Agent, or Firm* — Christopher R. Powers; Endress+Hauser (USA) Holding Inc.

(57) ABSTRACT

An analytical device for determining a measured variable dependent on the concentration of one or more constituents of a sample includes a decomposition reactor surrounded by an insulating tube, a heating apparatus, an oxygen production system including at least one oxygen permeable membrane, a housing, and a feed gas guiding system for supplying a feed gas to the at least one membrane of the oxygen production system. The feed gas guiding system includes a reaction space surrounding the at least one membrane and is connected with an inflow duct open to the environment such that at least two partitions are arranged coaxially within the insulating tube and surrounding the decomposition reactor, (Continued)

where the partitions subdivide an intermediate space arranged between the decomposition reactor and the insulating tube into annular chambers forming the feed gas guiding system, where the annular chambers are connected with one another by overflow openings.

15 Claims, 2 Drawing Sheets

(51) Int. Cl.
    *B01J 19/02*     (2006.01)
    *B01J 19/24*     (2006.01)
    *B01L 3/00*     (2006.01)
    *B01L 7/00*     (2006.01)
    *G01N 33/00*     (2006.01)

(52) U.S. Cl.
CPC ............... *B01L 3/502* (2013.01); *B01L 7/00* (2013.01); *G01N 33/004* (2013.01); *G01N 33/0037* (2013.01); *B01J 2219/0263* (2013.01); *B01L 2300/0832* (2013.01); *B01L 2300/1827* (2013.01); *B01L 2400/0487* (2013.01); *Y02A 50/20* (2018.01)

(58) Field of Classification Search
CPC .. G01N 31/12; G01N 33/0037; G01N 33/004; B01L 3/502; B01L 7/00; B01L 2300/0832; B01L 2300/1827; B01L 2400/0487; Y02A 50/245

See application file for complete search history.

(56) References Cited

U.S. PATENT DOCUMENTS

| | | | |
|---|---|---|---|
| 5,714,091 A | | 2/1998 | Mazanec et al. |
| 5,980,840 A | * | 11/1999 | Kleefisch ............. B01D 53/885 422/211 |
| 6,139,810 A | * | 10/2000 | Gottzmann .......... B01J 19/2425 422/608 |
| 2003/0077835 A1 | * | 4/2003 | Boursier Niutta ..... G01N 31/12 436/160 |

FOREIGN PATENT DOCUMENTS

| | | |
|---|---|---|
| DE | 202012102724 U1 | 10/2012 |
| DE | 102014111506 A1 | 2/2016 |
| EP | 0052988 B1 | 9/1986 |
| JP | 07-098308 A | 4/1995 |
| WO | 2016/023707 A1 | 2/2016 |

OTHER PUBLICATIONS

Search Report for German Patent Application No. 10 2014 111 506.6, German Patent Office, dated Mar. 3, 2015, 7 pp.

* cited by examiner

ANALYTICAL DEVICE FOR CONSTITUENTS OF A SAMPLE

CROSS-REFERENCE TO RELATED APPLICATIONS

The present application is related to and claims the priority benefit of German Patent Application No. 10 2014 111 506.6, filed on Aug. 12, 2014 and International Patent Application No. PCT/EP2015/066507, filed on Jul. 20, 2015 the entire contents of which are incorporated herein by reference.

TECHNICAL FIELD

The invention relates to an analytical device for determining a measured variable dependent on the concentration of one or more constituents, especially oxidizable constituents, of a sample.

BACKGROUND

Such a measured variable can be, for example, a concentration of one or more substances or an element, e.g. sulfur, chlorine or hydrogen, in the sample or a global parameter, such as the total organically bound carbon content (Total Organic Carbon, abbreviated TOC), a total content of carbon (organically and inorganically bound, abbreviated TC) or the total bound nitrogen (Total Nitrogen, abbreviated $TN_b$).

Known analytical devices for automated determining of such measured variables comprise a decomposition reactor, into which a solid, liquid or gaseous sample is metered. In the decomposition reactor, which can be embodied, for example, as a pyrolysis tube, the constituents of the sample are thermally decomposed. In such case, organically and inorganically bound carbon is converted to carbon dioxide $CO_2$, nitrogen to nitrogen oxide $NO_x$, sulfur to sulfur oxides $SO_2/SO_3$, chlorine to hydrochloric acid HCl and hydrogen to water $H_2O$. The gas, respectively gas mixture, occurring in such case is fed, with the assistance of a carrier gas flowing permanently through the decomposition reactor, through a drying- and absorber unit of a measuring system, which serves for determining the measured variable. The carrier gas, as a rule, also delivers the oxygen needed for reaction. In some applications, especially for analysis in the trace range, highly pure oxygen is used as reaction- and carrier gas. The measuring system includes one or more specific detectors, which serve to ascertain the fraction of the oxidation products relevant for the measured variable to be determined in the gas stream supplied to the detector. If it is desired, for example, to ascertain the TOC value of the sample, there serves as specific detector an infrared detector, which determines the $CO_2$ content of the gas stream, from which a measured value of the TOC value of the sample can be derived. For $TN_b$ determination, a $NO_x$ content of the gas stream can be determined by means of a chemiluminescence measurement.

The providing of oxygen as carrier gas, respectively as reaction partner, for the thermal decomposition of the samples occurs in conventional analytical devices usually via pressurized gas bottles, gas generators or by means of adsorbents. Disadvantageous in the case of these methods is, in such case, the required costs- and device complexity as well as, in the case of the application of adsorbents, the low degree of purity of the oxygen.

Known from DE 20 2012 102 724 U1 is an analytical device utilizing thermal decomposition. Included is a system for direct production of oxygen from surrounding air. Serving for this is a ceramic material with a perovskite structure. The ceramic material can be embodied, for example, as a membrane or as granular material, and has at high temperatures an oxygen ion conductivity. This oxygen ion conductivity permits a separation of the oxygen from the remaining components of the surrounding air, in that oxygen is selectively transported through the ceramic material. In order to heat the perovskite material to the temperature required for oxygen transport, the process heat of the analyzer oven is utilized, so that essentially no additional energy is required. There is, however, no particular embodiment given, with which a sufficient temperature of the perovskite material is attainable without requiring an additional energy source.

SUMMARY

An object of the present invention is to provide an analytical device of the above mentioned type, which, with compact construction, permits an energy saving oxygen production.

This object is achieved by an analytical device having the features recited in claim 1. Advantageous embodiments of the invention are set forth in the dependent claims.

The analytical device of the invention for determining a measured variable dependent on the concentration of one or more constituents, especially oxidizable constituents, of a sample, includes:
- a decomposition reactor having an oxygen feeding means for introduction of oxygen into the decomposition reactor and a gas outlet connecting the decomposition reactor with a measuring system;
- a heating apparatus for heating the decomposition reactor to a predetermined operating temperature;
- an oxygen production system comprising at least one oxygen permeable membrane, especially of a ceramic material;
- a housing, in which an insulating tube surrounding the decomposition reactor, the heating apparatus and the oxygen production system is arranged; and
- a feed gas guiding system for supplying a feed gas to the at least one membrane of the oxygen production system, wherein the feed gas guiding system includes a reaction space surrounding the at least one membrane and is connected with at least one inflow duct open to the environment of the analytical device;

characterized in that at least two partitions, especially tubular partitions, are arranged within the insulating tube coaxially relative to the tube axis of the insulating tube and surrounding the decomposition reactor, wherein the partitions subdivide an intermediate space arranged between the decomposition reactor and the insulating tube into annular chambers forming the feed gas guiding system, wherein the annular chambers are connected with one another by overflow openings.

Air from the environment of the housing of the analytical device can be fed through the inflow duct via the feed gas guiding system to the reaction space as feed gas. Because the feed gas guiding system is formed by annular chambers arranged within the insulating tube and consequently is arranged essentially completely within the insulating tube, the feed gas entering through the inflow duct into the feed gas guiding system can be heated by means of the heating apparatus of the analytical device sufficiently that additional heating of the membrane is not required. Rather, the heat transported to the membrane by convection by means of the feed gas and the heat radiation of the heating apparatus reaching the membrane are sufficient to heat the ceramic material of the membrane up to the temperature required for a sufficient oxygen ion conduction. Especially advantageous is that also no additional means, e.g. a supplemental heating or a heat exchanger, are used or required for warming the feed gas flow. Since the gas stream is heated alone by means of the heating of the analytical device used for the thermal decomposition, an energy saving operation of the analytical device with little structural space requirement is implemented.

A first of the annular chambers can form the reaction space containing the at least one membrane. A second of the annular chambers can serve as an inflow chamber of the feed gas guiding system and be connected with the inflow duct of the feed gas guiding system or form such.

One of the annular chambers, especially the annular chamber serving as reaction space, can be connected with the environment of the housing via at least one outflow opening led through the wall of the housing.

The outflow opening serves as outlet for the feed gas occurring as retentate of the oxygen production system and is preferably led out from the insulating tube.

The outflow opening can comprise at least one duct formed in a housing wall of the housing surrounding the insulating tube, wherein the housing wall is embodied to cool off feed gas flowing through the duct. For example, the housing wall can comprise a material of high thermal conductivity and be equipped with additional, active or passive, cooling elements, such as e.g. cooling fins as passive cooling elements, in order to assure a sufficient cooling of the feed gas, respectively feed gas retentate, coming from the oxygen production system, so that this can be given off into the environment without danger.

Advantageous is an embodiment, in the case of which the opening of the inflow duct to the environment of the housing is arranged in a lower region of the housing, spaced from one or more overflow openings opening in the upper region of the inflow chamber and connecting the inflow chamber with an additional annular chamber of the feed gas guiding system. This embodiment brings about, due to a chimney effect arising within the inflow chamber, a thermal convection, which transports cool air inflowing through the inflow duct and heated in the inflow chamber by means of the heating apparatus of the analytical device via the overflow opening into the additional chambers of the feed gas guiding system.

In an advantageous further development of this embodiment, the outflow opening opens in an upper region of the last annular chamber of the feed gas guiding system with reference to the flow direction of a feed gas flow flowing through the feed gas guiding system during operation of the analytical device. The last annular chamber can be, for example, the annular chamber serving as reaction space. This annular chamber is connected via one or more overflow openings arranged in a lower region of the annular chamber with an additional annular chamber of the feed gas guiding system, via which additional chamber the feed gas is supplied to it. Utilized in this embodiment is likewise a chimney effect arising within the outermost annular chamber for the transport of feed gas via the outflow opening into the environment.

The tubular partitions can advantageously be formed of a material, which is at least partially transparent for heat radiation, especially in the infrared region, so that the heat radiation outgoing from the heating apparatus can contribute to the heating of the membrane. An example of such a material is quartz glass.

The feed gas guiding system can have a heating chamber surrounding the heating apparatus. For example, one of the annular chambers of the feed gas guiding system can serve as a heating chamber, so that a feed gas flow flowing through the feed gas guiding system flows around the heating apparatus. Alternatively, the heating apparatus can, however, also be arranged outside of the feed gas guiding system. The heating apparatus can, for example, comprise a helically shaped, electrical heating element extending around the decomposition reactor, especially one arranged within the heating chamber.

Different arrangements provide options for the annular chambers. If the feed gas guiding system has a heating chamber, the annular chamber forming the reaction space can, for example, surround the annular chamber forming the heating chamber. Alternatively, it is also possible to have the annular chamber forming the heating chamber surround the annular chamber forming the reaction space. Additionally, the feed gas guiding system can comprise other coaxially arranged annular chambers, which respectively, in given cases, are divided by other, coaxially arranged, tubular partitions of the additional annular chambers and are connected with one another by overflow openings.

The feed gas is preferably air from the environment of the analytical device.

The mentioned measuring system can be a component of the analytical device. It includes at least one specific detector for registering the content of one or more predetermined compounds, e.g. $CO_2$ or $NO_x$, in a gas stream leaving the decomposition reactor via the gas outlet. Additionally, the measuring system can comprise an evaluation unit or be embodied for connection with an external evaluation unit. For example, the analytical device can comprise as specific detector for determining a TOC value an infrared detector embodied to produce a measurement signal dependent on the $CO_2$ content of the gas stream. Alternatively or supplementally, the analytical device can comprise a chemiluminescence detector (CLD detector) as specific detector for determining a $TN_b$ value. The specific detector for determining the $TN_b$ value can also be embodied to produce a measurement signal based on infrared detection or an electrochemical measurement. If the analytical device is an elemental analyzer, the measuring system can comprise a detector specific for the element to be determined, e.g. carbon, sulfur, nitrogen, hydrogen and/or chlorine. Such detectors are known per se in the state of the art.

The oxygen production system can be connected with the oxygen feeding means of the decomposition reactor for introduction of oxygen produced by the oxygen production system into the decomposition reactor, in order during operation of the analytical device to introduce the produced oxygen directly into the decomposition reactor.

The membrane of the oxygen production system can be embodied as a membrane tube closed at one end and having an outer retentate side facing the reaction space and an inner permeate side facing the interior of the tube. If there reigns on the permeate side a lesser oxygen partial pressure than on the retentate side, oxygen is transported from the feed gas present in the reaction space through the membrane into the interior of the membrane tube. Depending on the oxygen amount required for the decomposition, the oxygen production system can have a number of membranes embodied as membrane tubes. In an embodiment, the analytical device can have a number of membranes, especially a number of membranes embodied in such a manner as membrane tubes.

The interior of the membrane tube can be connected via a pump with the oxygen feeding means of the decomposition reactor. The pump can be embodied to produce in the interior of the tube a negative pressure relative to the pressure reigning in the reaction space, so that there is on the permeate side a lesser oxygen partial pressure than on the retentate side of the membrane.

The diameters and lengths of the annular chambers as well as the flow of the feed gas through the feed gas guiding system are so matched to the length of the membrane tube that during operation of the analytical device the tube has over the entire length of its section protruding into the reaction space a temperature, which is greater than a predetermined temperature threshold value, which corresponds to a minimum operating temperature of the membrane. If there are a number of membranes present, especially membranes formed as membrane tubes, the same holds for all membranes. The minimum operating temperature corresponds to a temperature, in the case of which a sufficient oxygen ion conductivity of the ceramic membrane material occurs. In the case of a ceramic, oxygen conducting, perovskite material, this temperature lies preferably above 500° C., especially preferably above 800° C.

In an embodiment, the annular breadth of the cross section of the reaction space, i.e. the difference between the inner radius and the outer radius of the cross section, amounts to 0.01 to 0.1 times the length of the section of the tube forming the membrane located within the reaction space. Typically, the membrane tube extends over almost the entire length of the reaction space, so that the annular breadth of the cross section of the reaction space amounts likewise, for instance, to 0.01 to 0.1 times the length of the reaction space.

BRIEF DESCRIPTION OF THE DRAWINGS

The invention will now be explained in greater detail based on the example of an embodiment illustrated in the drawing, the figures of which show as follows.

DETAILED DESCRIPTION

Figure 1:
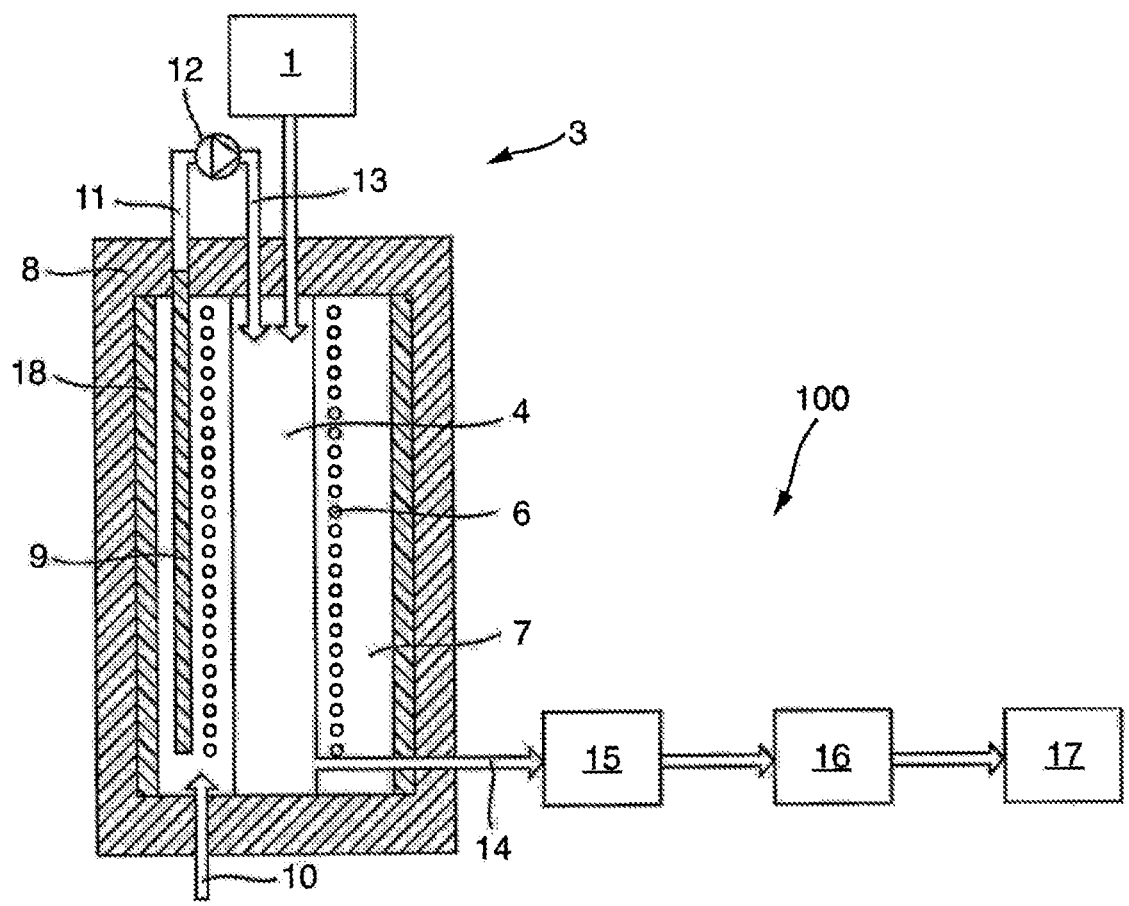
FIG. 1 shows a schematic representation of an analytical device.

The analytical device 100 includes a sample dosing or metering system 1, via which a substance to be examined is suppliable to a thermal decomposition system 3. Decomposition system 3 includes a tubular decomposition reactor 4, which is heatable by means of a heating apparatus 6. Heating apparatus 6 is embodied in the present example as an electrical resistance heater, which comprises a helically shaped heating element extending around the decomposition reactor. Decomposition system 3 is accommodated in a housing 8, in which is arranged also an oxygen production system with a number of oxygen permeable membranes 9 (in order to avoid clutter, only one membrane is shown in FIG. 1) and a feed gas guiding system 7 surrounding the decomposition reactor 4. Feed gas guiding system 7 is shown schematically in FIG. 1 and in greater detail in FIG. 2. Decomposition reactor 4, heating apparatus 6 and feed gas guiding system 7 are thermally insulated from the housing 8 by means of an insulating tube 18 surrounding them.

The membranes 9 are embodied in the present example as tubes formed of a ceramic material having oxygen ion conductivity. Suitable ceramic materials are, for example, oxides with perovskite structure. Perovskites are ternary oxides with lattice structure of $ABO_3$ type. Above a material dependent, minimum operating temperature, which can lie between 500 and 1000° C., these materials have simultaneously electrical conductivity and oxygen ion conductivity. Thus, it is possible to transport oxygen through a gas-sealed ceramic membrane, wherein the separation of the oxygen from other components of a feed gas (which can be, for example, air) supplied to the membrane occurs. If there reigns on the outside of the tubes (also referred to as the retentate side) a higher oxygen partial pressure than on the inner side (also referred to as permeate side) facing the interior of the tubes, then, at temperatures above the minimum operating temperature of the membrane, oxygen molecules on the retentate side are reduced to negatively charged, oxygen ions, oxygen ions are transported from the retentate side to the permeate side through the membrane and, on the permeate side, oxygen ions are oxidized to molecular oxygen. In this way, oxygen is transported through the membrane and separated from the other components of the feed gas remaining on the retentate side. Suitable materials are, for example, perovskite like oxides such as $Ba_{1-x}Sr_xCo_{1-y}Fe_yO_{3-\delta}$, especially e.g. $Ba_{0.5}Sr_{0.5}Co_{0.8}Fe_{0.2}$, or $La_{1-x}Sr_xCo_{1-y}Fe_yO_{3-\delta}$, especially e.g. $La_{0.2}Sr_{0.8}Co_{0.5}Fe_{0.5}O_{3-\delta}$, as well as nickel/cobalt perovskite oxide with the composition $La_{0.5}Sr_{0.5}Co_{0.8}Ni_{0.22}O_{3-\delta}$.

The membranes 9 embodied as tubes are sealed on one end. Their opposite ends are connected via a gas line 11 with a pump 12, which is embodied to produce in the interior of the tubes a negative pressure, so that there arises between retentate side and permeate side the oxygen partial pressure drop required for the oxygen transport. Introduced as feed gas in the example shown here is air from the environment of the analytical device 100 via the inflow duct 10 into the feed gas guiding system 7. Also a number of inflow ducts can be present. Here, in order to avoid clutter, only one inflow duct is shown.

By means of the pump 12, the gaseous oxygen occurring on the permeate side of the membranes 9 is introduced via the gas supply line 13 into the decomposition reactor 4. In such case, the oxygen serves simultaneously as a carrier gas and as an oxidizing agent for the constituents of the sample provided in the decomposition reactor via the sample dosing or metering system 1. The decomposition is performed at a temperature between 500 and 1000° C., which is achieved by means of the heating apparatus 6. The decomposition reactor includes besides the gas supply line 13 also a gas outlet 14, which connects the decomposition reactor 4 with a dryer 15. Dryer 15 is connected via a gas line with a detector 16, which is embodied to output a measurement signal dependent on the measured variable to be determined. In the present example of a TOC analytical device, the detector 16 can be an infrared detector, which is embodied to produce a measurement signal dependent on the $CO_2$ content of the gas stream supplied from the gas outlet 14 via the dryer 15 to the detector 16. Detector 16 is connected with an evaluation unit 17, which is embodied to register the measurement signal of the detector 16 and, based on the measurement signal, to ascertain a measured value of the measured variable, here the TOC value of the sample. The evaluation unit 17 can be, for example, an electronic data processing system, especially a PC, which includes, and can execute, an evaluation program serving to determine the TOC.

The oxygen production can occur according to need, wherein the oxygen flow can be matched to the respective requirements. The control of the oxygen production can be achieved based on the design of the membrane reactor, especially by selecting the number of membranes used, and by controlling the operating parameters, especially the partial pressure difference between permeate side and retentate side of the membranes 9. The analytical device 100 requires and uses no additional heating means or heat exchangers for heating the membranes 9 to a temperature above the minimum operating temperature. The heating apparatus 6 serving for heating the decomposition reactor 4 serves simultaneously for heating the membranes 9.

Figure 2:
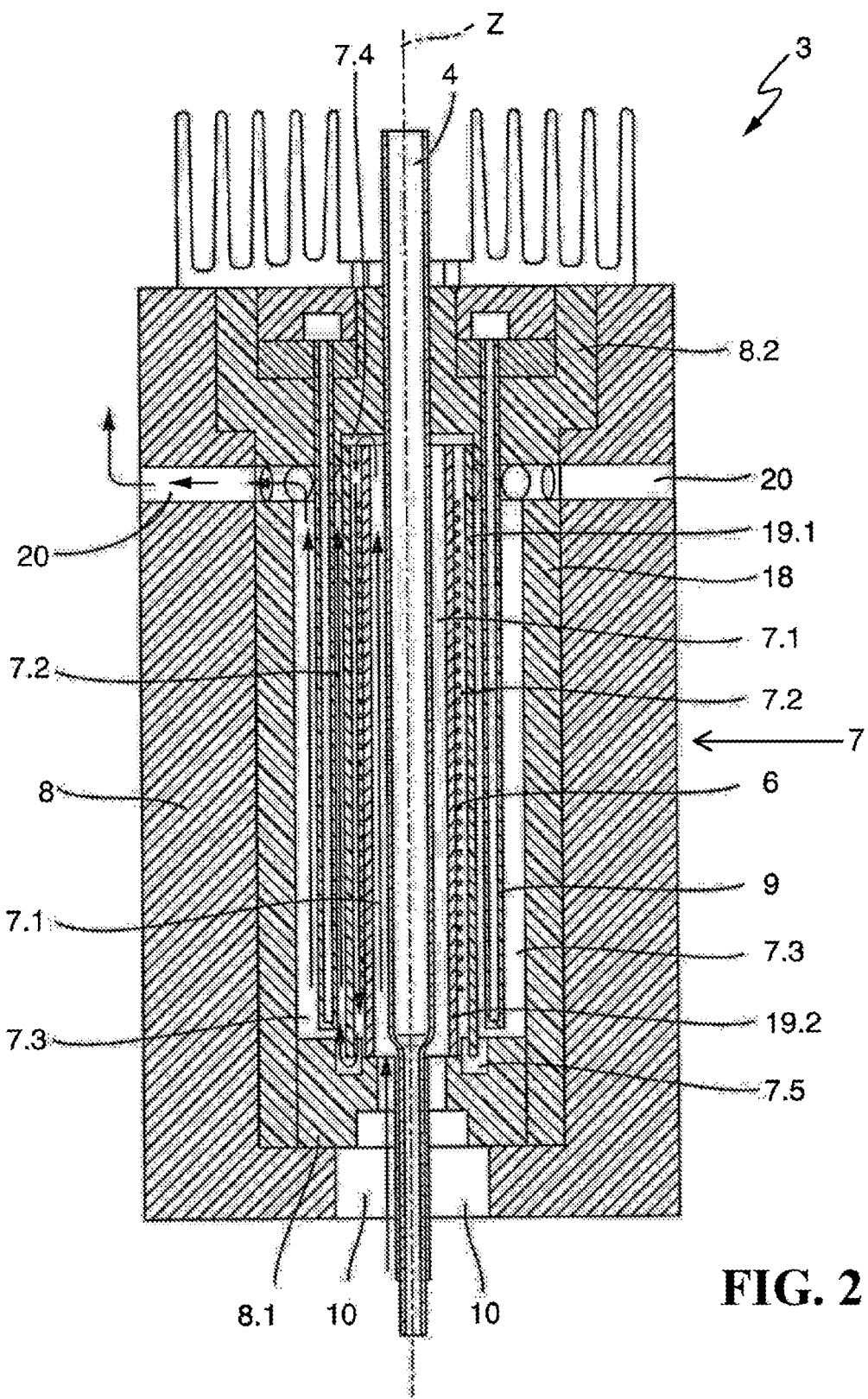
FIG. 2 shows a schematic longitudinal section through the decomposition reactor, the oxygen production system and the feed gas guiding system of the analytical device illustrated in FIG. 1.

FIG. 2 shows details of a possible embodiment of the feed gas guiding system 7 integrated in the thermal decomposition system 3 of the analytical device 100 illustrated in FIG. 1. Components identical with the system illustrated in FIG. 1 are provided with equal reference characters. Decomposition system 3 is essentially cylindrically symmetrically constructed and possesses a cylindrical symmetry axis Z, which coincides with the tube axis of the decomposition reactor 4 and of the insulating tube 18. Decomposition system 3 includes a cylindrical housing 8, which surrounds the decomposition reactor 4 and the feed gas guiding system 7. Cylindrical housing 8 is sealed on its oppositely lying end faces by inserts 8.1, 8.2. Decomposition reactor 4 and the feed gas guiding system 7 are thermally insulated from the housing 8 by means of an insulating tube 18. Two tubular partitions 19.1, 19.2, surrounding the decomposition reactor 4 and arranged coaxially relative to the cylindrical axis Z subdivide the annular space surrounding the decomposition reactor 4 and surrounded by the insulating tube 18 and the housing 8 into three annular chambers 7.1, 7.2, 7.3. The tubular partitions 19.1, 19.2 fit on their ends in such a manner into the inserts 8.1, 8.2 that a gas transport from one annular chamber to the other is only possible via the overflow ducts 7.4, 7.5. The partitions 19.1, 19.2 are made of a material, which at least partially transmits heat radiation of the heating apparatus 6. An example of a material suitable for the partitions 19.1, 19.2 is quartz glass.

The membranes 9 are secured in insert 8.2 as tubes closed at one end. They extend parallel to cylindrical axis Z through the outermost of the three annular chambers, annular chamber 7.3, wherein the length of the section of the membranes 9 arranged within the annular chamber 7.3 corresponds essentially to the axial length of the annular chamber 7.3. This annular chamber 7.3 bounded by the insulating tube 18 and the outer partition 19.1 forms the reaction space of the feed gas guiding system 7, in which oxygen on the (outer) retentate side of the membranes 9 is reduced to oxygen ions, which can be transported through the membranes 9 to the (inner) permeate side of the membranes 9, such as described above. The outer annular chamber 7.3 is connected with the environment via outflow openings 20 extending radially relative to the cylindrical axis Z through the wall of the housing 8. These outflow openings 20 are embodied as ducts and serve as a retentate outlet.

Arranged in the annular chamber 7.2 located between the outer partition 19.1 and the inner partition 19.2 is the heating apparatus 6. In the example shown here, a helically shaped heating element is arranged in this annular chamber 7.2 and surrounds the partition 19.2 and simultaneously also the decomposition reactor 4. Annular chamber 7.2 forms, thus, the heating chamber of the feed gas guiding system 7. The innermost annular chamber 7.1 bounded by the partition 19.2 and the wall of the decomposition reactor 4 is connected via the inflow ducts 10 of the feed gas guiding system 7 with the surrounding atmosphere.

In operation of the analytical device 100, a feed gas flow forms between the inflow openings 10 and the outflow openings 20 serving as retentate outlet. This feed gas flow extends in the direction of the arrows, first of all, through the innermost annular chamber 7.1 between the decomposition reactor 4 and the partition 19.2 of the heating chamber, where the inflowing cold air begins to be heated. Via the overflow ducts 7.4, the feed gas flow then enters the heating chamber 7.2 and is there led over the windings of the heating element, so that the feed gas is heated further. The gas stream extends further via the overflow ducts 7.5 into the reaction space 7.3, where the heated feed gas by convection together with the heat radiation passing through the partitions 19.1, 19.2 from the heating apparatus 6 to the membranes 9 heats the membranes 9 over their entire length arranged in the reaction space 7.3 to a temperature, which lies above their minimum operating temperature. In the interior of the tubular membranes 9, a negative pressure is produced by means of pump 12, so that, such as already described, an oxygen transport occurs through the membranes 9. The gas mixture remaining in the reaction space, the retentate, is discharged into the environment through the outflow openings 20. While flowing through the outflow openings 20, the gas mixture cools down, so that it can be given off to the surrounding atmosphere without problem.

The length and annular breadth of the annular chambers of the feed gas guiding system, the length and number of membranes and the flow of the feed gas flow are preferably matched to one another in such a manner that the membranes achieve their minimum operating temperature over the entire length of their sections extending through the reaction space. In the present example, the annular cross section of the outermost annular chamber 7.3, thus of the reaction space containing the membranes 9, has, for example, an annular breadth (=difference between outer- and inner diameters) of 5 to 20 mm in the case of a lengthwise dimension of the space between 100 to 500 mm. The cross section of the heating chamber formed by the middle annular chamber 7.2 has in the present example an annular breadth of 1 to 5 mm in the case of lengthwise dimension equal to that of the outermost annular chamber 7.3. The innermost annular chamber 7.1 can have dimensions similar to those of the middle annular chamber 7.2, i.e. a cross section having an annular breadth of 1 to 5 mm and a length between 100 and 500 mm. With the described construction, with 6 to 12 membranes 9, an oxygen flow of about 50 ml/min to 10 l/min can be achieved.

Variations of the example of an embodiment illustrated here can be considered, which are likewise subject matter of the invention described here. For example, an option is to arrange the heating apparatus in an outer annular chamber and to arrange the membranes in an inner annular chamber surrounded by the annular heating chamber. The gas stream passes also in this embodiment from one or more inflow ducts through the heating chamber into the reaction space. This arrangement is advantageous, when the thermal decomposition is to be performed in presence of a catalyst, which can lead to the fact that the decomposition reactor is heated to a temperature, which lies even below the minimum operating temperature of the membranes. It is in additional embodiments, moreover, also possible to provide other annular chambers or other routing of the feed gas flow.

The invention claimed is:

1. An analytical device for determining a measured variable dependent on the concentration of one or more constituents of a sample, comprising:
   a decomposition reactor including an oxygen feeding means for introducing oxygen into the decomposition reactor and a gas outlet connecting the decomposition reactor with a measuring system, the decomposition reactor at least partially surrounded by an insulating body;

a heating apparatus for heating the decomposition reactor to a predetermined operating temperature;

an oxygen production system including at least one oxygen permeable membrane;

a housing in which the insulating body, the decomposition reactor, the heating apparatus and the oxygen production system are arranged; and a feed gas guiding system for supplying a feed gas to the at least one membrane of the oxygen production system, the feed gas guiding system including a reaction space at least partially surrounding the at least one membrane, and connected to at least one inflow duct in fluid communication with the environment of the analytical device, and further including at least two partitions arranged within the insulating body and substantially coaxially relative to the insulating body, the partitions surrounding the decomposition reactor, wherein the partitions divide an intermediate space defined between the decomposition reactor and the insulating body into annular chambers, wherein the annular chambers are in fluid communication with one another via overflow openings.

2. The analytical device of claim 1, wherein one of the annular chambers defines the reaction space, the reaction space in fluid communication with the environment of the housing via at least one outflow opening extending through a wall of the housing.

3. The analytical device of claim 2, wherein the outflow opening includes at least one outflow duct formed in the wall of the housing, wherein the wall is embodied to cool the feed gas outflowing from the feed gas guiding system through the outflow duct.

4. The analytical device of claim 1, wherein one of the annular chambers is embodied as an inflow chamber in fluid communication with the inflow duct, the inflow duct having an inflow opening in fluid communication with the environment of the housing, the inflow opening disposed in a lower region of the housing and spaced from one or more overflow openings disposed in an upper region of the inflow chamber, the one or more overflow openings connecting the inflow chamber with another annular chamber of the feed gas guiding system.

5. The analytical device of claim 2, wherein at least one outflow opening opens into an upper region of a last annular chamber of the feed gas guiding system, relative to a flow direction of a feed gas flow through the feed gas guiding system during operation of the analytical device, the last annular chamber in fluid communication with another annular chamber via at least one overflow opening disposed in a lower region of the last annular chamber and spaced from the outflow opening of the upper region of the last annular chamber.

6. The analytical device of claim 1, wherein the partitions are of a material that is at least partially transparent to heat radiation.

7. The analytical device of claim 1, wherein the heating apparatus is disposed in one of the annular chambers of the feed gas guiding system.

8. The analytical device of claim 1, wherein the oxygen production system is connected to the oxygen feeding means of the decomposition reactor such that oxygen produced by the oxygen production system is introduced into the decomposition reactor.

9. The analytical device of claim 1, wherein the membrane is embodied as a membrane tube closed at one end and having an outer surface facing the reaction space and an inner surface facing an interior of the membrane tube.

10. The analytical device of claim 9, wherein the interior of the membrane tube is in fluid communication with the oxygen feeding means of the decomposition reactor via a pump, the pump embodied to generate a negative pressure within the membrane tube relative to a pressure in the reaction space.

11. The analytical device of claim 9, wherein widths and lengths of the annular chambers and the flow of the feed gas through the feed gas guiding system are selected relative to a length of a section of the membrane tube disposed within the reaction space such that, during operation of the analytical device, the membrane tube has a temperature over the length of the section disposed within the reaction space, the temperature being greater than a predetermined temperature threshold value, which corresponds to a minimum operating temperature of the membrane.

12. The analytical device of claim 11, wherein the reaction space has a cross-sectional annular breadth of about 0.01 to 0.1 times the length of the section of the membrane tube disposed within the reaction space.

13. The analytical device of claim 1, wherein the at least one membrane is composed of a ceramic material.

14. The analytical device of claim 1, wherein the insulating body and the at least two partitions are tubular.

15. The analytical device of claim 1, wherein the measured variable is dependent on the concentration of one or more oxidizable constituents of the sample.

* * * * *